(12) United States Patent
Jeffress

(10) Patent No.: US 6,739,209 B1
(45) Date of Patent: May 25, 2004

(54) AUTOMATED SAMPLE ANALYSIS SYSTEM

(76) Inventor: Colin Roy Jeffress, 12 Mataro Road, Hope Valley (AU), 5090

( * ) Notice: Subject to any disclaimer, the term of this patent is extended or adjusted under 35 U.S.C. 154(b) by 186 days.

(21) Appl. No.: 10/049,060

(22) PCT Filed: Aug. 9, 2000

(86) PCT No.: PCT/AU00/00947

§ 371 (c)(1),
(2), (4) Date: Feb. 7, 2002

(87) PCT Pub. No.: WO01/11342

PCT Pub. Date: Feb. 15, 2001

(30) Foreign Application Priority Data

Aug. 9, 1999 (AU) .................................. 2099

(51) Int. Cl.[7] .............................................. G01N 1/00
(52) U.S. Cl. ...................................... 73/865.8
(58) Field of Search ................... 73/866, 865.8, 73/863.91, 863.92, 864.81; 250/339.1, 339.11, 339.12, 339.14, 339.15, 338.1, 341.8

(56) References Cited

U.S. PATENT DOCUMENTS 4,014,255 A   3/1977   Fox 4,550,768 A  * 11/1985  McMullen et al. ......... 164/456

FOREIGN PATENT DOCUMENTS

| CA | 2022275 | 1/1992 |
|---|---|---|
| DE | 36 01 932 | 10/1986 |
| JP | 60-89732 | 5/1985 |
| JP | 07-043319 | 2/1995 |
| JP | 07-294427 | 11/1995 |

* cited by examiner

*Primary Examiner*—Robert Raevis
(74) *Attorney, Agent, or Firm*—Young & Thompson

(57) ABSTRACT

A sample analyser for bulk materials such as sugar cane includes a shredding means which finelly divides the material and deposits a sample on an endless conveyor (2). The sample is compressed and its upper surface (30) is levelled, to ensure a fixed presentation height relative to the reading head of an analyser (48) such as an infrared spectrometer. A plate (20) may be used to control the presentation height of a moving sample. Alternatively, the sample may be deposited in compartments mounted on the conveyor, smoothed mechanically or manually, and then moved beneath the analyser (48). Each sample is placed on top of the remnant, if any, of a previous sample, thus preventing contamination of the upper surface (30) by the latter.

16 Claims, 3 Drawing Sheets

AUTOMATED SAMPLE ANALYSIS SYSTEM

CROSS REFERENCE TO RELATED APPLICATION

This is the 35 USC 371 national stage of International Application PCT/AU00/00947 filed on Aug. 9, 2000, which designated the United States of America.

FIELD OF THE INVENTION

This invention concerns an automated sample analysis system.

BACKGROUND OF THE INVENTION

The present system will be described in relation to biological material specifically sugarcane but those skilled in the art would appreciate that timber forage, animal products, food products generally including raw and processed materials are handled by such systems. The system may be modified to handle plastics, rubber and mineral products. The analysis utilises a near infra red (NIR) spectometer but ultrasound, microwave, nuclear irradiation and capacitative testing devices are described in the literature. It is useful if the system is capable of receiving input from control or recognition devices and controlling other devices as part of its place in a production or information chain.

It is customary for a growers' payment to depend on the extractable sugar. The grower can be penalised or rewarded of the factors such as excess fibre and impurities.

Mills commonly provide laboratories adjacent the growers' truck entry to the Mill where samples are prepared manually by appropriate grinding. Wet chemistry processes follow and a result is generated in 4–8 hours. Automating such a process presents a variety of problems, typically the creation of a physical form which can be read by the testing device. A sample must be representative of the tissue extract. It must be presented suitably for a reading to emerge. The current sample must not be contaminated by the previous sample. The sample must be disposed of so that a new reading is obtainable. The procedure must offer precision in reading and require minimal human supervision. Preferably the apparatus should be automated as by logic circuit or micro processor control.

WO 93/15470 describes a system suitable for monitoring coal input to electricity generating stations. A motor driven, endless conveyor drives multiple coal samples beneath a linear array of sensors. It stops and starts to give each sensor in turn exposure to the sample. Infrared, microwave and gamma ray radiation are utilised to give information about the ratio of C—H to O—H bonds; free moisture and S/H/O ratios. A mathematical matrix is generated and thereafter coefficients are calculated.

Biological materials present additional problems. A sample carrying fruit juice, blood or other adhesive liquid tends to contaminate subsequent samples.

SUMMARY OF THE INVENTION

The apparatus aspect of this invention provides apparatus for radiation analysis of finely divided test material comprising a radiation sensor and means capable of conveying the sample past the sensor at a controlled presentation height and surface condition. Preferably the apparatus performs spectrographic analysis of samples of finely divided biological material and comprises a spectrographic sensor and means capable of conveying the sample past the sensors such that the surface of the sample remains at a predetermined reading distance from the sensor. Usually the apparatus utilises predetermined factors. For some materials adjustment may be necessary and therefore control is useful.

DESCRIPTION OF THE DRAWINGS

In order that the present invention can be clearly understood and put into practical effect the description will now refer to the drawings which show non-limiting embodiments of the invention, wherein.

DETAILED DESCRIPTION OF THE DRAWINGS

Version 1

Figure 1:
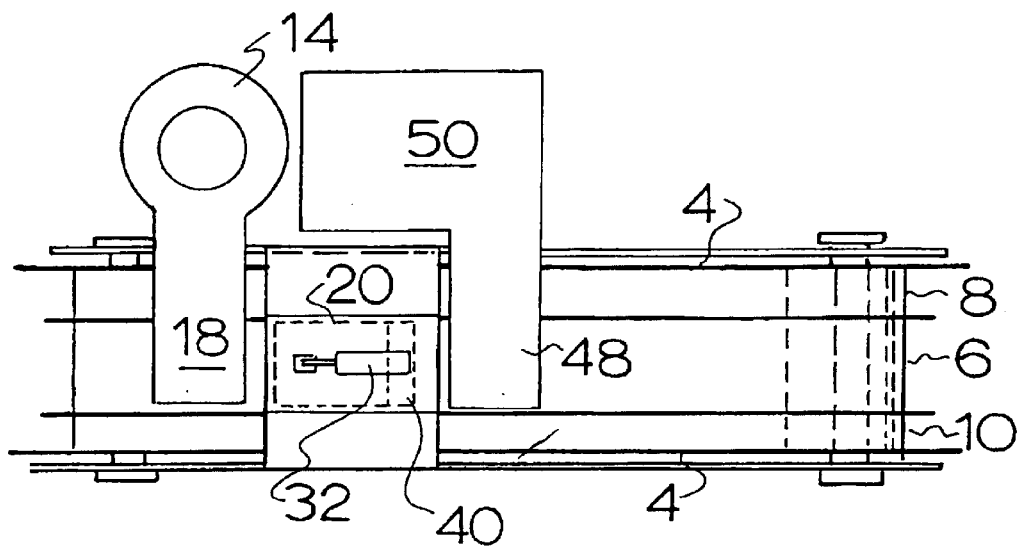
FIG. 1 is a plan of the apparatus.
Figure 2:
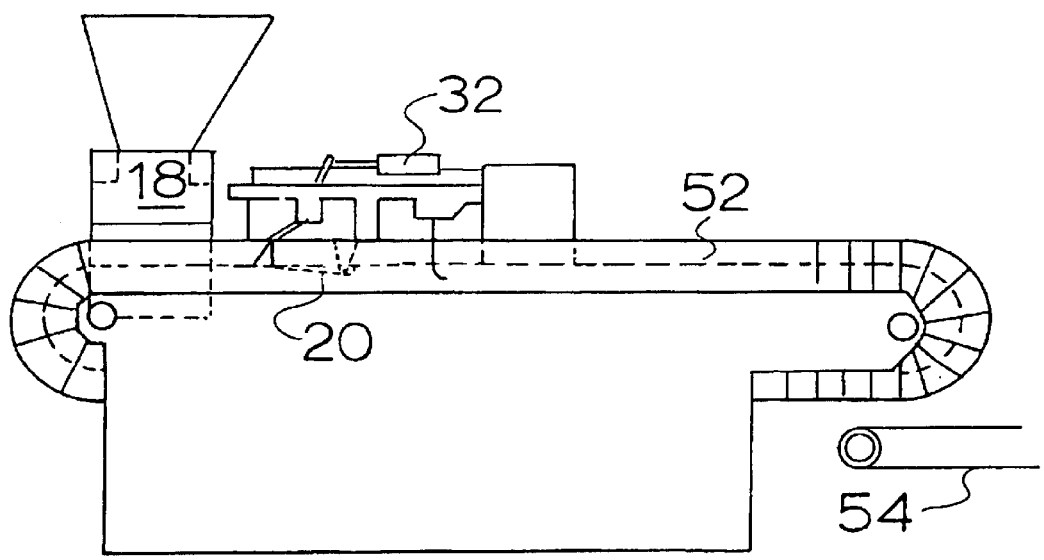
FIG. 2 is a side elevation.
Figure 3:
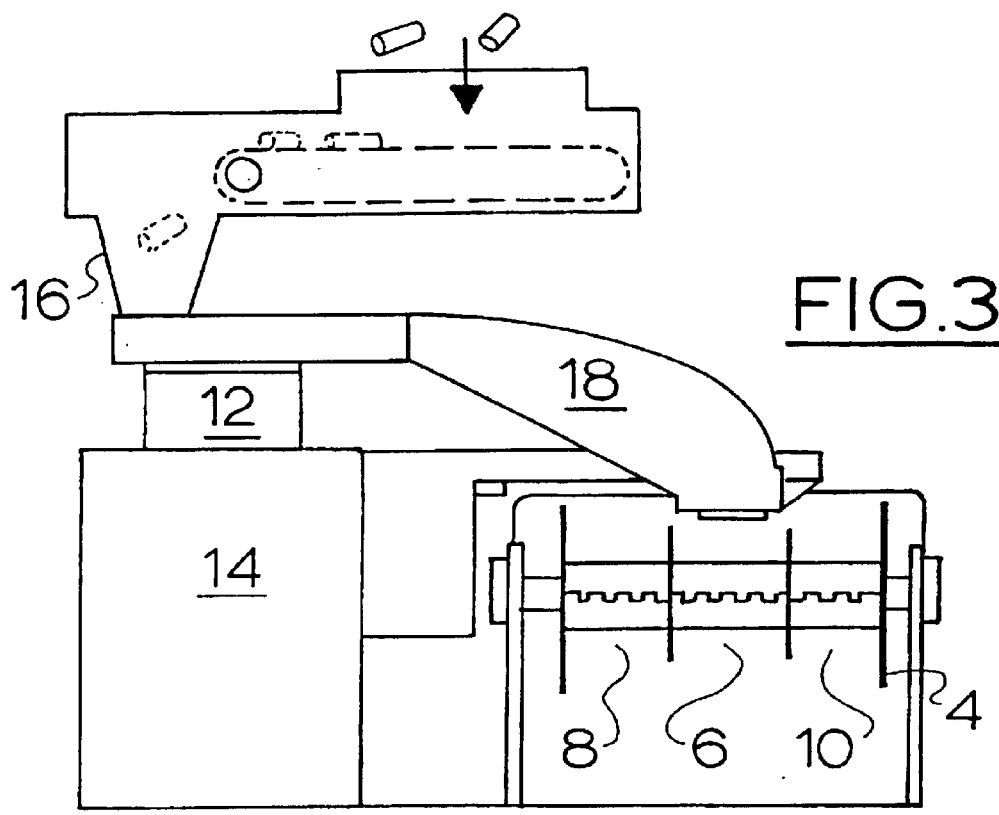
FIG. 3 is an end elevation.

The apparatus is an enclosed unit intended to function at a sugar mill adjacent the truck entry to the Mill. The unit contains an infeed section and fibrator, a cane presentation conveyor, a NIR reading system, electronic and mechanical control systems and a disposal system which discharges to a bin.

Referring now to the drawings 1 to 4, an endless conveyor 2 has four rows of interleaved side guards 4 which define a central sample channel 6 and a pair of adjacent deeper overflow channels 8, 10. The conveyor is driven by an electric motor at an adjustable feed speed of 0.5–2 m/min.

Figure 4:
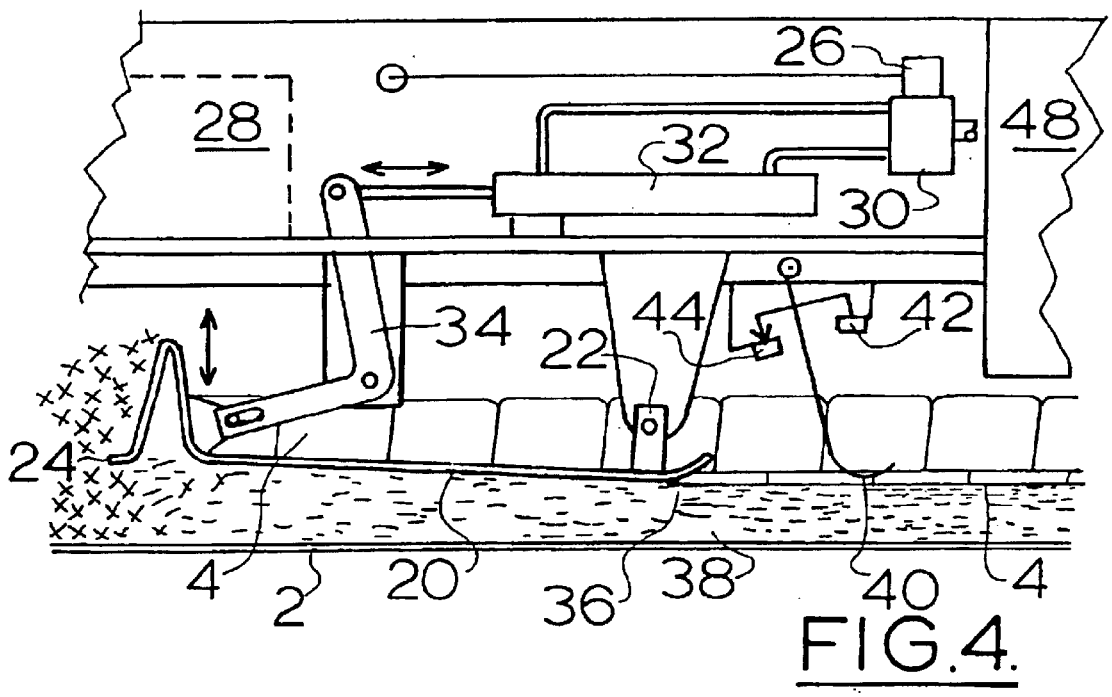
FIG. 4 is an enlarged side view of the sensor and depth regulator zone in FIG. 2.

The fibrator is a rotary cutter 12 driven by a three phase brake motor 14. The cane pieces constituting the sample drop from an infeed conveyor 16 where the cutter reduces them to needle-shaped fibres 10–15 mm long. Centrifugal force expels the cane as a stream of fibres containing the sugar components which the cutting operation exposes but all juice is retained. The fibrated samples is directed by the diverter 18 into the sample channel 6. An uneven layer of sample fibres builds progressively on the moving conveyor. The conveyor advances the fibre mass towards the depth regulator which comprises a stainless steel plate 20 (see FIG. 4) which is free to tilt about a horizontal hinge axis 22. The leading end of the plate carries an upstanding blade 24 which diverts the excess into the overflow channels 8, 10.

A solenoid 26 above the plate 20 receives 24 vdc pulses at 10 Hz from the controller 28. The solenoid operates shuttle valve 30 which reverses air supply to ram 32. The ram reciprocates plate 20 through crank 34. The plate settles the pile into a carpet whose depth is fixed by the arcuate heel 36 at the trailing hinge end of the plate. The heel and plate together with the conveyor surface and the side guards create a carpet 38 of precise dimension and packing density.

As the carpet advances, a flap sensor 40 senses the advancing edge of the carpet. Contact 42 opens and contact 44 closes. They signal the adjacent NIR reading head 48 to begin reading the advancing material. The NIR spectrometer in console 50 is a stand alone "direct light" instrument FOSS TECATOR (Sweden) with the reading head 48 connected by a fibre bundle. The spectrometer requires constant temperature enclosure and non-interruptible power supply. For this purpose the apparatus has an air conditioned cabinet to house the instrument and electronics at 24° C. A compressed air supply and vortex cooler provide auxiliary cooling. These components are not shown in the drawings.

As the carpet height diminishes the flap sensor drops and readings cease. Contacts 42, 44 operate to switch off the solenoid and speed up the conveyor. The carpet travels undisturbed well beyond the reading head into zone 52 before falling off the conveyor. This prevents cracks or voids in the part of the carpet being read. The conveyor dumps the sample onto a separate conveyor 54 which takes it to a waste bin (not shown). A typical sample cycle is 3 minutes. The console 50 houses the power supply, interface board, relay outputs and control circuitry for the spectrometer. A strip printer delivers the numerals and codes which record the contents of the sample identifying batch/grower and the like. The information is stored in a database and recorded for further analysis.

Figure 5:
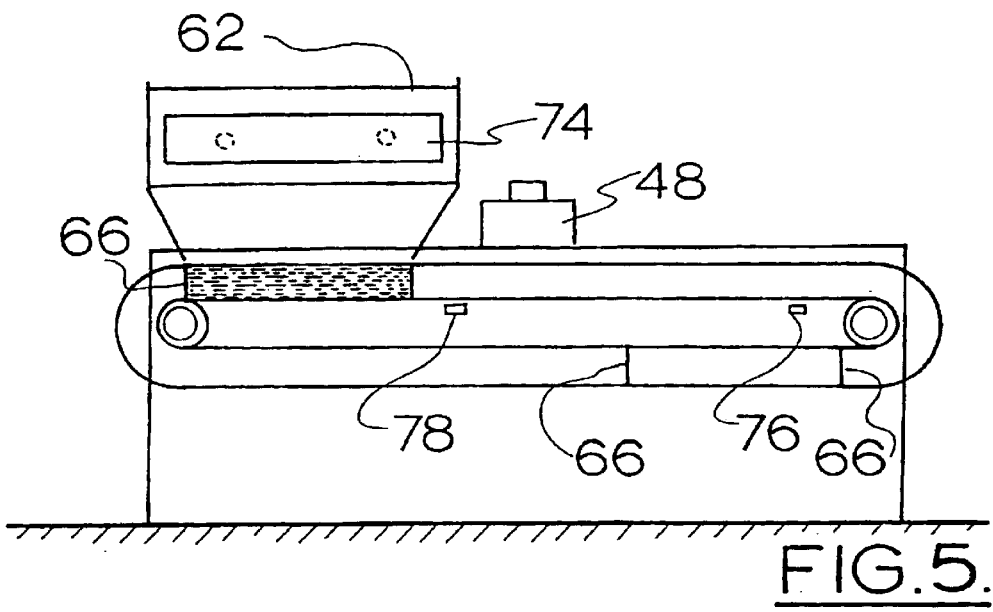
FIG. 5 is a diagrammatic side elevation of an alternative version.
Figure 6:
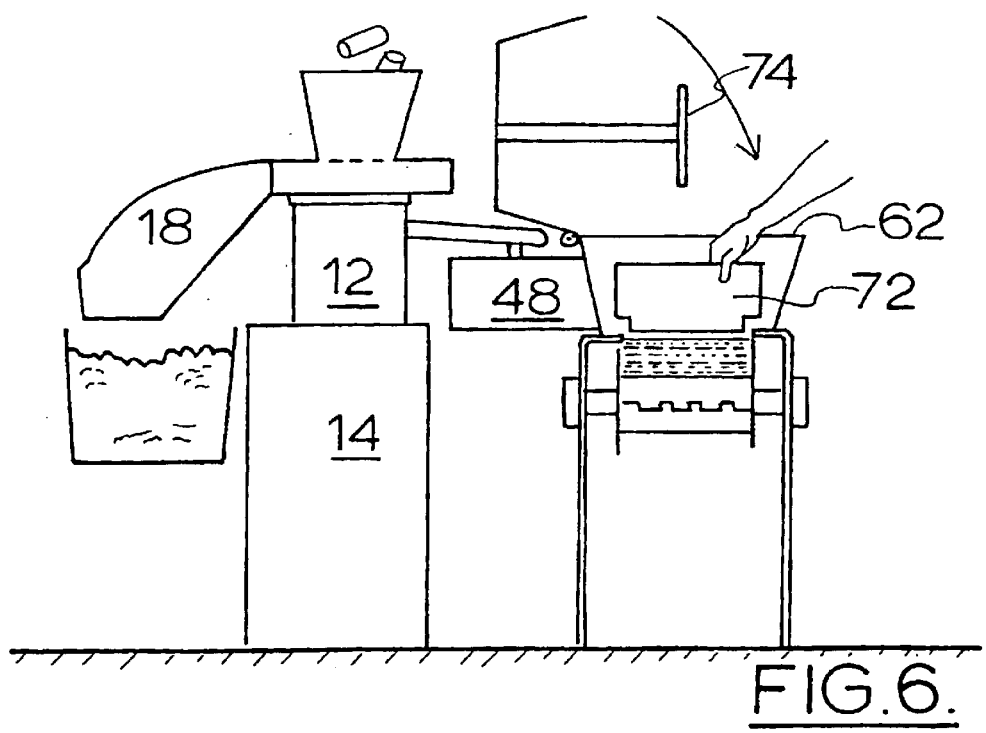
FIG. 6 is a diagrammatic end elevation of FIG. 5.

Version 2

Where rapid multiple readings are needed, say of the order of a minute, a small apparatus is used which has no integral fibrator. Referring now to FIGS. 5 and 6, a motorized shredder of suitable capacity generates fibrated cane material from 200 mm pieces and these are loaded onto the feed box 62 conveyor of the machine by hand using a scoop. A conveyor channel has four transverse walls 66 which create two compartments about 800×150×45 mm between the walls 66. The feed box 62 is filled manually. The feed box delivers shredded material neatly into the first compartment as shown. At an operators signal, the conveyor advances. The operator levels the compartment with a blade 72. A controlled tamping plate 74 descends on the compartment imposing predetermined packing density on the sample i.e. the ratio of voids to solids is the same in each cycle. The conveyor advances between automatic stops 76, 78. The sensor head 48 is located over the filled compartment and scans the surface of the material. At the end of the cycle the conveyor advances, dumping the contents of the first compartment.

In a non-illustrated version, two conveyors lie side by side and reading head swings from one to the other.

We have found the advantages of the version 1 to be:
1. the vastly quicker procedure compared to wet chemistry methods;
2. reliable comparison between samples is possible;
3. more economical than a conventional laboratory;
4. a fresh surface is available for reading because it lies on top of any previous sample remnant;
5. environmentally friendly through the reduction or elimination of harmful chemical waste resulting from wet chemistry methods.

Whilst the above has been given by way of illustrative example of the present invention many variations and modifications thereto will be apparent to those skilled in the art without departing from the broad ambit and scope of the invention as set out in the appended claims.

The claims defining the invention are as follows:

1. Apparatus for radiation analysis of samples of finely divided biological material comprising a sensor, a depth regulator and means capable of conveying the sample past the sensor such that the upper surface of the sample remains at a predetermined reading distance from the sensor, wherein the depth regulator cooperates with the conveyor to deflect excess material and present a carpet of sample material of predetermined height, density and surface condition to the sensor.

2. The apparatus as claimed in claim 1 wherein the depth regulator is a plate having a leading edge and a trailing edge beneath which the material is, in use, constrained to pass, by the conveyor movement.

3. The apparatus as claimed in claim 2 wherein the plate is hinged near the trailing edge to define with the conveyor surface a tapered zone of consolidation.

4. The apparatus as claimed in claim 3 wherein the plate has means capable of vibrating the plate in order to assist consolidation.

5. The apparatus as claimed in claim 4 wherein the vibrating means operates at 5–15 Hertz.

6. The apparatus as claimed in claim 2 including means capable of detecting the presence of the material to be sampled located between the plate and the sensor.

7. The apparatus as claimed in claim 1 including the means capable of detecting the presence of the material to be sampled located downstream of the sensor.

8. The apparatus as claimed in claim 1 wherein only part of the width of the conveyor is dedicated to the movement of the sample, the excess material being free to spill laterally on the remaining width of the conveyor.

9. The apparatus as claimed in claim 1 wherein a sample depositor located upstream of the depth regulator lays new sample material on the conveyor so as to cover any remnant of the previous sample eliminating measurement errors which could result from cross contamination between samples.

10. The apparatus as claimed in claim 1 wherein the conveyor has a channel extending over part of its width capable in use of confining the sample material and an adjacent channel for overspill.

11. The apparatus as claimed in claim 1 wherein the conveyor has surface mounted compartments which are chargeable to a predetermined controlled reproducible height and means to advance each compartment to a reading position beneath the sensor.

12. The apparatus as claimed in claim 11 wherein a compression plate is capable of exerting predetermined controlled tamping pressure on the sample in the compartment prior to reading.

13. The apparatus as claimed in claim 11 wherein the conveyor is endless and a dumping station is located downstream of the sensor.

14. An apparatus according to claim 1 being fully automated for sample analysis of bulk materials comprising a fibrator for finely dividing the material to be analysed, a conveyor downstream of the fibrator for presenting the sample in conjunction with the depth regulator at a predetermined controlled height with a predetermined controlled surface condition, the sensor detecting properties of the sample by radiation and data processing means for calculating and presenting data derived from the sensor.

15. The apparatus according to claim 1 wherein the conveyor is an endless conveyor.

16. The apparatus according to claim 1 wherein the depth regulator comprises a manually operable leveller followed by a tamping device applying a predetermined packing density on the sample.

* * * * *